United States Patent
Nixon et al.

(10) Patent No.: US 6,376,541 B1
(45) Date of Patent: Apr. 23, 2002

(54) UPREGULATION OF ENDOGENOUS PROSTAGLANDINS TO LOWER INTRAOCULAR PRESSURE

(75) Inventors: Jon C. Nixon; Karen C. David, both of Mansfield, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/445,320

(22) PCT Filed: Nov. 4, 1999

(86) PCT No.: PCT/US99/26068

§ 371 Date: Dec. 6, 1999

§ 102(e) Date: Dec. 6, 1999

(87) PCT Pub. No.: WO00/27424

PCT Pub. Date: May 18, 2000

Related U.S. Application Data

(60) Provisional application No. 60/107,450, filed on Nov. 6, 1998, now abandoned.

(51) Int. Cl.$^7$ .......................................... A61K 31/557
(52) U.S. Cl. ...................... 514/530; 514/573; 514/913; 424/85.1; 424/85.2
(58) Field of Search ................................ 514/530, 573, 514/913, 912, 922; 424/85.2

(56) References Cited

U.S. PATENT DOCUMENTS

| | | | |
|---|---|---|---|
| 4,235,771 A | 11/1980 | Adam et al. | 260/112.5 |
| 5,260,059 A | 11/1993 | Acott et al. | 424/94.67 |
| 5,321,128 A | 6/1994 | Stjernschantz et al. | 514/530 |
| 5,565,492 A | 10/1996 | DeSantis et al. | 514/530 |
| 5,698,733 A | 12/1997 | Hellberg et al. | 560/56 |
| 5,700,835 A | 12/1997 | Dean et al. | 514/530 |
| 5,721,273 A | 2/1998 | Sallee et al. | 514/530 |
| 5,770,580 A | 6/1998 | Ledley et al. | 514/44 |

FOREIGN PATENT DOCUMENTS

| | | |
|---|---|---|
| EP | 0 561 073 A1 | 9/1993 |
| WO | WO 91/16917 | 11/1991 |
| WO | WO 98/24468 | 6/1998 |

OTHER PUBLICATIONS

Opthalmology 1993, Jan.; 100(1):9–14. Miller JW, Stinson WG, Folkman J. Regression of experimental iris neovascularization with systemic alpha interferon.*

Woodward, et al., "Intraocular pressure effects of selective prostanoid receptor agonists involve different receptor subtypes according to radioligand binding studies," *Journal of Lipid Mediators*, 6:545–553 (1993).

Woodward, et al., "Molecular Characterization and Ocular Hypotensive Properties of the Prostaglandin EP2 Receptor," *Journal of Ocular Pharmacology and Therapeutics* 11(3):447–454 (1995).

Waterbury, et al., "$EP_3$ but not $EP_2$ FP or TP Prostanoid–Receptor Stimulation May Reduce Intraocular Pressure," *Investigative Ophthalmology and Visual Science*, 31(12):2560–2567 (1990).

Weinreb, Polansky, Alvarado and Mitchell, "Arachidonic acid metabolism in human trabecular meshwork cells," *Invest Ophthalmol Vis Sci* 29:1708–12 (1988).

Weihreb and Mitchell, "Prostaglandin production by cultured cynomolgus monkey trabecular.meshwork cells" *Prostaglandis, Leukotrienes, and Essential Fatty Acid* from Cultured Human, 36:97–100 (1989).

Kerstetter et al., "Prostaglandin $F_{2\alpha}$–1–Isopropylester Lowers Intraocular Pressure Without Decreasing Aqueous Humor Flow," *American Journal of Ophthalmology* 105:30–34 (1988).

Nakajima, Goh, Azuma & Hayaishi, "Effects of Prostaglandin $D_2$ and its analogue BW245C, on Intraocular Pressure in Humans," *Graef's Arch Clin Exp Ophthalmol* 229:411–413 (1991).

Polansky, Kurtz, Alvarado and Weinreb, "Eicosanoid production and glucocorticoid regulatory mechanisms in cultured human trabecular meshwork cells." In: Bito, L.Z., Stjernschantz, J. eds, *The ocular effects of prostaglandins and other eicosanoids*. New York: Alan R Liss. 113–38 (1989).

Giuffre, The Effects of Prostaglandin $F_{2\alpha}$ the Human Eye, *Graefe's Archive Ophthalmology* 22:139–141 (1985).

Habenicht, Goerig, Grulich, Rothe, Gronwald,Loth, Schettier, Kommerell, and Ross, "Human Platelet–derived Growth Factor Stimulates Prostaglandin Synthesis by Activation and Rapid De Novo Synthesis of Cyclooxygenase," *J. Clin. Invest.* 75:1381–1387 1985).

Ichikawa, Sugimoto and Negishi, "Molecular aspects of the structures and functions of the prostaglandin E receptors," *J. Lipid Mediators Cell Signaling*, 14:83–87 (1996).

Bito, "A physiological approach to glaucoma management: The use of local hormones and pharmacokinetics of prostaglandin esters." In: Bito, L.Z., Stjernschantz, J. eds. *The ocular effects of prostanoids and other eicosanoids*, New York: Alan R. Liss. 329–47 (1989).

Flach and Eliason, "Topical Prostaglandin $E_2$ Effects on Normal Human Intraocular Pressure," *Journal of Ocular Pharmacology* 4(1):13–18 (1988).

(List continued on next page.)

*Primary Examiner*—Prema Mertz
*Assistant Examiner*—Sarada C Prasad
(74) *Attorney, Agent, or Firm*—Barry L. Copeland

(57) ABSTRACT

A method of lowering intraocular pressure (IOP) employs an upregulating agent that induces increased prostaglandin synthesis in the eye. The method of treatment entails administering to the eye of a mammal in need thereof a prostaglandin upregulating agent to increase endogenous prostaglandin synthesis and thereby effect a reduction in intraocular pressure. In a preferred embodiment the upregulating agent is IL-1.

9 Claims, No Drawings

OTHER PUBLICATIONS

Gerritsen, Weinstein, Gordon and Southren, "Prostaglandin Synthesis and Release from Cultured Human Trabecular-meshwork Cells and Scleral Fibroblasts," *Exp. Eye Res.* 43:1089–1102 (1986).

Alm, "The Potential of Prostaglandin Derivatives in Glaucoma Therapy," *Current Opinion in Ophthalmology*, 4(11):44–50 (1993).

Bhattacherjee and Henderson, "Inflammatory responses to intraocular injected interleukin–1," *Cur Eye Res* 6:929–934 (1987).

Bill, "Uveoscleral drainage of aqueous humor: Physiology and pharmacology." In: Bito, L.Z., Stjernschantz, J. eds. *The ocular effects of prostanoids and other eicosanoids*. New York: Alan R. Liss. 417–27 (1989).

Samples, et al., "Cytokines lower intraocular pressure and product cyclitis," *Investigative Ophthalmology & Visual Science* 36(4):S735 (1995) XP000907355.

Tashjian, Jr., et al., "α and β human transforming growth factors stimulate prostaglandin production an bone resorption in cultured mouse calvaria" *Proc. Natl. Acad. Sci. USA* 82(13):4535–4538 (1985) XP–000907310.

Opthalmology 1993, Jan; 100(1):9–14. Miller JW, Stinson WG, Folkman J. Regression of experimental iris neovascularization with systemic alpha interferon.*

Bito, "Glaucoma: a physiologic perspective with Darwinian overtones," *J. Glaucoma*, 1:193–205 (1982).

Fidler, Nii, Utsugi, Brown, Bakouche and Kleinerman, "Differential release of TNF–α, IL–1, and $PGE_2$ by human blood monocytes subsequent to interaction with different bacterial derived agents," *Lymphokine Res*, 9(4):449–463 (1990).

Kimball, Clark, Schneider and Persico, "Enhancement of in vitro lipopolysaccharide–stimulated interleukin–1 production by levamisole," *Clin Immunol Immunopathol*, 58:385–398 (1991).

Kimball, Schneider,Fisher and Clark, "Levamisole causes differential cytokine expression by elicited mouse peritoneal macrophages," *J Leukoc Biol*, 52:349–356 (1992).

Maeda, Knowles and Kleinerman, "Muramyl tripeptide phosphatidylethanolamine encapsulated in liposomes stimulates monocyte production of tumor necrosis factor and interleukin–1 in vitro," *Cancer Commun*, 3(10/11):313–321 (1991).

Medvedev, Fuks, Bovin and Zemlyakov, "The immunomodulating activity of new muramyl dipeptide derivatives in vitro," *Biull Eksp Biol Med*, 114(12):1838–1841 (1992).

Sarih, Souvannavong and Adam, "Differential stimulation of macrophages for tumor cytostasis and monokine production," *Cancer Lett*, 64:187–194 (1992).

* cited by examiner

UPREGULATION OF ENDOGENOUS PROSTAGLANDINS TO LOWER INTRAOCULAR PRESSURE

This application is a 371 of PCT/US99/26068 filed Nov. 4, 1999, which claims benefit of Provisional Ser. No. 60/107,450 filed Nov. 6, 1998, abandoned.

TECHNICAL FIELD

The present invention relates to methods of lowering intraocular pressure (IOP), such as in the treatment of glaucoma. The invention particularly relates to the upregulation of the endogenous synthesis of prostaglandins in the eye to effect such treatment.

BACKGROUND OF THE INVENTION

Glaucoma

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior segment of the eye. The anterior segment of the eye consists of anterior and posterior chambers. The anterior chamber lies in front of the iris and contains aqueous humor which helps support the cornea. The posterior chamber lies behind the iris and encompasses the crystallin lens of the eye.

The causes of aqueous humor accumulation in the anterior segment are not fully understood. It is known that elevated intraocular pressure ("IOP") can be at least partially controlled by administering drugs such as beta-blockers and carbonic anhydrase inhibitors, which reduce the production of aqueous humor within the eye, or agents such as miotics and sympathomimetics, which increase the outflow of aqueous humor from the eye.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have been associated with serious pulmonary side effects attributable to their effects on beta-2 receptors in pulmonary tissue. Sympathomimetics, on the other hand, may cause tachycardia, arrhythmia and hypertension.

Prostaglandins

Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-Series prostaglandins (EP 0 561 073 A1). Two naturally-occurring prostaglandins which have been shown to lower IOP are $PGF_{2\alpha}$ (an F-series prostaglandin) and $PGE_2$ (an E-series prostaglandin) which have the following chemical structures:

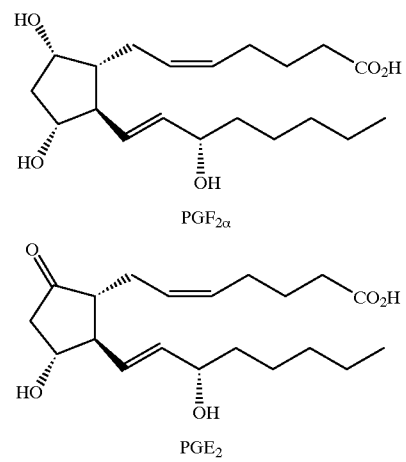

$PGF_{2\alpha}$ $PGE_2$

The relationship of $PGF_{2\alpha}$, receptor activation and IOP lowering effects is not well understood. It is believed that $PGF_{2\alpha}$, receptor activation leads to increased outflow of aqueous humor. Regardless of the mechanism, $PGF_{2\alpha}$, and certain of its analogs have been shown to lower IOP (Giuffre, The Effects of Prostaglandin $F_{2\alpha}$ the Human Eye, *Graefe's Archive Ophthalmology* 222:139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology* 105:30–34 (1988)). Thus, it has been of interest in the field to develop synthetic $PGF_{2\alpha}$, analogs with IOP lowering efficacy.

Synthetic $PGF_{2\alpha}$-type analogs have been pursued in the art (*Graefe's Archive Ophthalmology* 229:411–413 (1991)). Though $PGF_{2\alpha}$ type molecules lower IOP, a number of these types of molecules have also been associated with undesirable side effects resulting from topical ophthalmic dosing. Such effects include an initial increase in IOP, breakdown of the blood aqueous barrier and conjunctival hyperemia (Alm, The Potential of Prostaglandin Derivatives in Glaucoma Therapy, *Current Opinion in Ophthalmology*, 4(11):44–50 (1993)).

The relationship between EP receptor activation and IOP lowering effects is not well understood. There are currently four recognized subtypes of the EP receptor: ($EP_1$, $EP_2$, $EP_3$, and $EP_4$ (Ichikawa, Sugimoto, Negishi, Molecular aspects of the structures and functions of the prostaglandin E receptors, *J. Lipid Mediators Cell Signaling*, 14:83–87 (1996)). It is known in the art that ligands capable of $EP_2$ receptor activation, such as $PGE_2$ and synthetic analogs (Flach, Eliason, Topical Prostaglandin $E_2$ Effects on Normal Human Intraocular Pressure *Journal of Ocular Pharmacology* 4(1):13–18 (1988); Woodward, et al., Molecular Characterization and Ocular Hypotensive Properties of the Prostaglandin EP2 Receptor *Journal of Ocular Pharmacology and Therapeutics* 11(3):447–454 (1995)), or $EP_3$ receptor activation (Woodward, et al., Intraocular pressure effects of selective prostanoid receptor agonists involve different receptor subtypes according to radioligand binding studies, *Journal of Lipid Mediators*, 6:545–553 (1993); Waterbury, et al., EP$_3$ but not EP$_2$ FP or TP Prostanoid-Receptor Stimulation May Reduce Intraocular Pressure, *Investigative Ophthalmology and Visual Science*, 31(12):2560–2567 (1990)) lower IOP. However, some of these molecules have also been associated with undesirable side effects resulting from topical ophthalmic dosing, including an initial increase in IOP, photophobia, and eye ache (see for example Flach, Eliason, Topical Prostaglandin E$_2$ Effects on Normal Human Intraocular Pressure, *Journal of Ocular Pharmacology* 4(1):13–18 (1988)).

It has now been postulated that ocular hyperemia, such as that attendant to the topical administration of the prostaglandins described above, is mediated by a sensory nerve response on the surface of the eye [1]. The prostaglandins PGF$_{2\alpha}$ and PGE$_2$ are naturally formed by different tissues in the eye and are components of normal aqueous humor. Nevertheless, both are associated with acute inflammation and are considered early mediators of an induced inflammatory response. Still, co-administration of these natural prostaglandins to reduce IOP has been proposed. See, U.S. Pat. No. 5,565,492.

Many synthetic prostaglandins purporting to avoid or reduce one or more of the side effects attributable to the natural prostaglandins have also been shown to lower IOP by varying degrees. See, for example, U.S. Pat. Nos. 5,321,128; 5,698,733; 5,700,835; and 5,721,273.

The cornea, which is reportedly capable of producing both PGF$_{2\alpha}$ and PGE$_2$, appears also to have the ability to convert topically applied PGF$_{2\alpha}$, into PGE$_2$ to elevate aqueous humor levels of this important prostaglandin. In fact, prostaglandins are believed to be produced in all tissues surrounding the anterior chamber of the human eye including the iris/ciliary body, lens epithelial pocket and trabecular meshwork. Constitutive prostaglandin synthesis (non-inducible and providing relatively constant prostaglandin levels in normal aqueous humor) by these tissues may be an important factor in the normal control of IOP, and the loss of prostaglandin synthetic capability at or near the anterior chamber could result in an increase in IOP. Based in part on these observations, it is suggested that tissues in contact with the anterior chamber are likely accustomed to rapid changes in, and probably accommodate to, elevated levels of prostaglandins in aqueous humor.

Since prostaglandins, both naturally occurring and synthetic, exogenously applied to the cornea, lower IOP in the glaucoma patient, the availability of a critical concentration of a naturally occurring prostaglandins at or near the "target site(s)" of action is likely diminished over time during the course of the disease. This is one basis for the current prostaglandin therapy for the treatment of glaucoma. The presumed target(s) of prostaglandins are postulated to be related to an altered outflow mechanism associated with possible structural modifications through the uveal-scleral tract or trabecular meshwork. For purposes of this discussion, the mode of action of prostaglandins is of secondary importance to that of sustaining the critical concentration of prostaglandins, at or near the target site in the anterior chamber, adequate to lower and control IOP. Current prostaglandin therapies require chronic topical dosing and are, to varying degrees, attended by one or more of the side-effects discussed above.

Studies by Gerritsen et al. [15] first demonstrated that certain agents such as bradykinin, leukotriene C$_4$, acetylcholine, histamine, Ionophore A23187 and arachidonic acid could all stimulate PGE$_2$ synthesis in cultured trabecular-meshwork cells. Confirmation of the work on stimulation with bradykinin has been reported by Weinreb and Mitchell with cultured monkey trabecular meshwork cells [16]. In this same study these authors also report a dose dependent down regulation of PGE$_2$ synthesis with dexamethasone. Moreover, platelet-derived growth factor (PDGF), a protein known to induce mitogenesis in fibroblasts and commonly associated with the wound healing environment, stimulates PGE$_2$ synthesis 10–15 fold in these cells and in the presence of exogenous arachidonic acid, the stimulation by PDGF increases to 28 fold [17], Moreover, in Swiss 3T3 fibroblasts, it has been shown that PDGF achieves this stimulation indirectly by inducing the synthesis of cyclooxygenase. Thus, a large array of molecules (both in size and known pharmacology) are known to be effective in directly or indirectly modulating endogenous prostaglandin (primarily PGE$_{2\alpha}$) synthesis. However, the use of such upregulating agents in the treatment of glaucoma and ocular hypertension, and their advantages over conventional therapies has not heretofore been suggested in the art.

SUMMARY OF THE INVENTION

The present invention is directed to a method of treating, ameliorating or preventing the occurrence of glaucoma or elevated intraocular pressure (IOP) in the eye of a mammal. The method comprises administering to the eye a therapeutically effective amount of an agent that upregulates endogenous synthesis of one or more IOP-lowering prostaglandins.

A related aspect of the present invention is a pharmaceutical composition, which comprises a pharmaceutically acceptable carrier and a therapeutically effective amount of an aforementioned upregulating agent. Preferably, the composition, when administered to an affected eye, will directly or indirectly elevate the level of i) lnterleukin-1 (IL-1) in the aqueous humor or in the anterior chamber of the eye; ii) Transforming Growth Factor (TGF)-beta 1 or 2 in the aqueous humor or in the anterior chamber of the eye; or iii) the density of IL-1 or TGF beta receptors in the anterior chamber, and especially in the trabecular meshwork cells.

DETAILED DESCRIPTION OF THE INVENTION

The present invention involves a method of treating the eyes of a mammal suffering from a glaucomatous condition, wherein the intraocular pressure (IOP) of the eye is or is likely to become elevated above its "normal" state. The present method can be employed to reduce, or ameliorate elevated IOP and to prevent or impede increases in normal IOP, thereby controlling or slowing the progression of the disease.

A method of the present invention comprises administering to an eye of the mammal a therapeutically effective amount of a prostaglandin upregulating agent. As used herein, the term "upregulating agent" means any agent which, directly or indirectly, induces increased synthesis of a prostaglandin in the eye to effect a reduction of intraocular pressure. The method of the present invention may be practiced with any agent which directly or indirectly upregulates prostaglandin synthesis in the eye. Preferred among such upregulating agents are IL-1 beta (Genzyme, Mass., USA), TGF-beta 1 or 2 (Oncogene Research Products, Cambridge, Mass., USA), levamisole (Flavine International, Inc., Closter, N.J., USA), muramyl dipeptide (MDP) (Glycotech Corporation, Rockville, Md., USA) (see also U.S. Pat. No. 4,235,771, the disclosure of which is incorporated herein by reference), and muramyl tripeptide (MTP).

Other ingredients which may be desirable to use in the ophthalmic preparations of the present invention include preservatives, co-solvents, and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Some upregulating agents of the present invention may have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methyl cellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

EXAMPLE 1

Induction of Prostglandin Synthesis in Human Corneal Fibroblasts By IL-1 Alpha Primary human corneal fibroblasts were grown in culture from freshly denuded corneal stromal tissue from a 55-year old male donor. Cells (passage 4) were seeded into 12-well plates and grown to 80% confluency. Selected cells were then exposed to Interleukin-1 alpha (10 ng/ml final) in Ham's F-10 Nutrient mixture (HyClone Corporation) containing 10% fetal bovine serum by medium replacement in the wells. Control cells received medium devoid of this inflammatory cytokine. Cells were then incubated in a 37° C., 5% $CO_2$, humidified incubator for 24 hours. Conditioned medium was then removed, centrifuged to remove any cellular debris (3 minutes at 2600 rpm and 4° C.), and analyzed for $PGE_2$ and $PGF_{2\alpha}$ levels in the medium using specific enzyme immunoassay kits (Cayman Scientific). Cells in each well were counted, and prostaglandin levels normalized to the cell count for the respective wells.

The results of this study, detailed in Table 1, clearly indicate that the presence of IL-1 alpha stimulates a dramatic elevation of the levels of both $PGE_2$ (>47 fold) and $PGF_{2\alpha}$ (>3 fold). These data support the premise of the present invention that cytokines like IL-1 alpha or others, including small synthetic molecules, which are known to act on cells through receptor mediated signal transduction, can lead to a significant elevation of extracellular levels of prostaglandins, especially $PGE_2$.

TABLE 1

INTERLEUKIN-1 ALPHA STIMULATION OF PROSTAGLANDIN $E_2$ AND PROSTAGLANDIN $F_{2\alpha}$ IN CULTURED HUMAN CORNEAL FIBROBLASTS

| | PROSTAGLANDIN PRODUCED PER 100,000 CELLS IN 24 HOURS (PICOGRAMS MEAN ± STD DEV) | |
| --- | --- | --- |
| TREATMENT | $PGE_2$ | $PGF_{2\alpha}$ |
| UNSTIMULATED | 1028 ± 484 | 525 ± 184 |
| 10 ng/ml INTERLEUKIN-1α | 48,736 ± 3597 | 1704 ± 367 |

EXAMPLE 2

Induction of Prostaglandin $E_2$ Synthesis in Cultured Human Trabecular Meshwork Cells By IL-1 BETA and/or TGF-BETA 1

Primary human trabecular meshwork cells were grown in culture according to the method of Weinreb, et al. [14] from an 18-year old donor. Cells (passage 5) were seeded into 12-well plates and grown until they just reached confluency, with culture medium replacement every 3–4 days. Triplicate wells of cells were then exposed to interleukin-1 beta (10 ng/ml final), TGF-beta 1 (10 ng/ml final) or both in 1 ml of Ham's F-10 Nutrient Mixture (Gibco-BRL), containing 2 mM L-glutamine and 0.4 mg/ml bovine serum albumin (Sigma Chemical Co.). Control cells received medium devoid of IL-1β and TGF-β1. Cells were then incubated in a 37° C., 5% $CO_2$, humidified incubator for 17 hours. $^{14}C$-arachidonic acid (300,000 dpm) was added to each well, and the cells were returned to the incubator for an additional 4 hours. A modified Bligh & Dyer lipid extraction [Can. J. Biochem. Physiol. 37,911 (1959)] was then performed on the cells and supernatants. An aliquot of the extracted samples and fatty acid standards were spotted on a moderate hardness silica gel thin-layer chromatography plate (Alltech K5, 20×20 cm, 250 μm thick). The plate was developed in prostaglandin TLC solvent (11:5:2:10 ethyl acetate: 2,2,4-trimethylpentane: acetic acid: distilled water), air-dried, and standard bands were visualized with vaporization of iodine crystals. Each lane on the plate was divided into segments based upon the position of the standards, and each segment was scraped off of the plate with a razor blade into a glass scintillation vial. Opti-fluor scintillation cocktail (Packard) was added to each vial, and the samples were counted on a beta scintillation counter. The amount of each fraction was calculated as a percentage of total counts per minute (CPM) from that sample.

The results of this study, detailed in Table 2, show that both TGF-β1 and IL-1β increase $PGE_2$ synthesis by cultured human trabecular meshwork cells. TGF-B1β increases $PGE_2$ synthesis by 74% over a non-treated control. Moreover, IL-1β increases $PGE_2$ synthesis by 440% over the control. The combination of TGF-1β and IL-1β unexpectedly yielded a total increase in $PGE_2$ synthesis of 590% over the control.

TABLE 2

| TREATMENT | % OF TOTAL CPM IN PGE2 FRACTION (MEAN ± STD DEV) | P VALUE |
|---|---|---|
| CONTROL | 1.73 ± 0.07 | |
| TGF-β1 (10 ng/ml) | 3.01 ± 0.38 | 0.011 |
| IL-1β (10 ng/ml) | 9.34 ± 0.70 | 0.001 |
| TGF-β1 + IL-1β | 11.93 ± 1.64 | 0.004 |

The present invention has been described with reference to certain embodiments for purposes of clarity and understanding. It should be appreciated that various improvements and modifications can be practiced within the scope of the appended claims and equivalents.

REFERENCES

The pertinent disclosures of the following references are incorporated herein by reference.

1. Kimball, E. S., Schneider, C. R., Fisher, M. C. and Clark, M. C., Levamisole causes differential cytokine expression by elicited mouse peritoneal macrophages. *J Leukoc Biol* (1992) 52:349–356.
2. Kimball, E. S., Clark, M. C., Schneider, C. R. and Persico, F. J., Enhancement of in vitro lipoplysaccharide-stimulated interleukin-1 production by levamisole. *Clin Immunol Immunopathol* (1991) 58:385–398.
3. Medvedev, A. E., Fuks, B. B., Bovin, N. V. and Zemliakov, A. E., The immunomodulating activity of new muramyl dipeptide derivatives in vitro. *Biull Eksp Biol Med* (1992) 114(12):1838–1841.
4. Sarih, M., Souvannavong, W. and Adam, A., Differential stimulation of macrophages for tumor cytostasis and monokine production. *Cancer Lett* (1992) 64:187–194.
5. Maeda, M., Knowles, R. D. and Kleinerman, E. S., Muramyl tripeptide phosphatididylethanolamine encapsulated in liposomes stimulates monocyte production of tumor necrosis factor and interleukin-1 in vitro. *Cancer Commun* (1991) 3:313–321.
6. Fidler, I. J., Nii, A., Utsugi, T., Brown, D., et al., Differential release of TNF-alpha, IL-1 and PGE2 by human blood monocytes subsequent to interaction with different bacterial derived agents. *Lymphokine Res* (1990) 9:449–463.
7. Bhattacherjee, P. and Henderson, B., Inflammatory responses to intraocularly injected interleukin-1. *Cur Eye Res* (1987) 6:929–934.
8. Weinreb, R. N., Polansky, J. R., Alvarado, J. A. and Mitchell, M. D., Arachidonic acid metabolismin human trabecular meshwork cells. *Invest Ophthalmol Vis Sci* (1988) 29:1708–12.
9. Polansky, J. R., Kurtz, R. M., Alvarado, J. A., and Weinreb, R. N., Eicosanoid production and glucocorticoid regulatory mechanisms in cultured human trabecular meshwork cells. In: Bito, L. Z., Stjernschantz, J. eds. *The ocular effects of prostaglandins and other eicosanoids.* New York: Alan R Liss. 1989:113–38.
10. Bill, A., Uveoscleral drainage of aqueous humor: Physiology and pharmacology. In: Bito, L. Z., Stjernschantz, J. eds. *The ocular effects of prostanoids and other eicosanoids.* New York: Alan P. Liss. 198 :417–27.
11. Bito, L. Z., A physiological approach to glaucoma management: The use of local hormones and pharmacokinetics of prostaglandin esters. In: Bito, L. Z., Stjernschantz, J. eds. *The ocular effects of prostanoids and other eicosanoids,* New York: Alan R. Liss. 1989:329–47.
12. Bito, L. Z., Glaucoma: a physiologic perspective with Darwinian overtones. *J Glaucoma* (1992) 1:193–205.
13. U.S. Pat. No. 5,770,580.
14. Weinreb, R. N. and Mitchell, M. D., Prostaglandin production by cultured cynomolgus monkey trabecular meshwork cells. *Prostaglandins, Leukotrienes, and Essential Fatty Acids* (1989) 36:97–100.
15. M. E. Weinstein, W. I., Gordon, G. G. and Southren, A. L., Prostaglanding Synthesis and Release from Cultured Human Trabecular-meshwork Cells and Scleral Fibroblasts. Exp. Eye Res. (1986) 43:1089–1102.
16. Weinreb R. N. and Mitchell, M.D., Prostagalnding Production by cultured Cynomolgus Monkey Trabecular Meshwork Cells. *Prostaglandins Leuko and Essent Fatty Acids* (1989) 36:97–100.
17. Haenicht, A. J. R., Goerig, M., Grulich, J., Rothe, D., Gronwald, R., Loth, U., Schettier, G., Kommerell, B. and Ross, R., Human Platelet-derived Growth Factor Stimulates Prostaglandin Synthesis by Activation and Rapid De Novo Synthesis of Cyclooxygenase. *J. Clin. invest.* (1985) 75:1381–1387.

What is claimed is:

1. A method of treating glaucoma or elevated intraocular pressure in an eye of a human comprising topically administering to the eye a therapeutically effective amount of a non-prostanoid prostaglandin upregulating agent that induces endogenous prostaglandin synthesis in said eye to effect a reduction in intraocular pressure.

2. The method of claim 1, wherein the upregulating agent is selected from the group consisting of: interleukin-1, transforming growth factor—beta 1, transforming growth factor—beta 2, platelet derived growth factor, levamisole, muramyl dipeptide, and muramyl tripeptide.

3. The method of claim 2, wherein the upregulating agent comprises interleukin-1.

4. A pharmaceutical composition comprising an ophthalmically acceptable carrier and an intraocular pressure lowering effective amount of a prostaglandin upregulating agent of claim 1.

5. The composition of claim 4, wherein the upregulating agent is selected from the group consisting of: interleukin-1, transforming growth factor—beta 1, transforming growth factor—beta 2, platelet derived growth factor, levamisole, muramyl dipeptide, and muramyl tripeptide.

6. The composition of claim 5, wherein the upregulating agent comprises IL-1.

7. The method of claim 1, wherein the prostaglandin upregulating agent effects upregulation of a prostaglandin selected from the group consisting of: $PGE_2$ and $PGF_{2\alpha}$.

8. The method of claim 7, wherein the upregulating agent effects upregulation of $PGE_2$.

9. The method of claim 7, wherein the upregulating agent effects upregulation of $PGF_{2\alpha}$.

* * * * *